United States Patent [19]
Vincent et al.

[11] 4,123,531
[45] Oct. 31, 1978

[54] ANTI-CONVULSANT N-ETHANOLAMINE DIPHENYL ACETAMIDES

[75] Inventors: Michel Vincent, Bagneux; Georges Remond, Versailles; Michel Laubie, Vaucresson; Jean-Claude Poignant, Bures, Yvette, all of France

[73] Assignee: Science Union et Cie, Societe Francaise de Recherche Medicale, Suresnes, France

[21] Appl. No.: 745,032

[22] Filed: Nov. 26, 1976

[30] Foreign Application Priority Data

Dec. 3, 1975 [FR] France ................................ 75 36918

[51] Int. Cl.$^2$ ................. A61K 31/165; A61K 31/495; C07D 295/08; C07D 295/10
[52] U.S. Cl. ............................... 424/250; 260/293.73; 260/293.76; 260/326.43; 260/558 R; 260/558 S; 260/559 D; 424/267; 424/274; 424/324
[58] Field of Search ....... 260/558 R, 501.19, 268 TR, 260/326.43, 268 BC, 293.73, 293.76; 424/324, 267, 250, 316, 274

[56] References Cited

U.S. PATENT DOCUMENTS 2,634,274  4/1953  Krimmel ...................... 260/558 R X

FOREIGN PATENT DOCUMENTS 2,161,011  7/1973  France.
2,176,473  11/1973  France.
1,170,274  11/1969  United Kingdom.

OTHER PUBLICATIONS

Zaugg et al., J. Amer. Chem. Soc. 72, pp. 3004–3007 (1950).
Agre et al., CA 51:2602b (1957).
Vincent et al., CA 82:4029g (1975).

Primary Examiner—Winston A. Douglas
Assistant Examiner—Thomas A. Waltz
Attorney, Agent, or Firm—Omri M. Behr

[57] ABSTRACT

This invention relates to novel acetamides, the nitrogen of which is substituted with an amino lower alkyl chain.

This invention also relates to a process for producing the said N-substituted acetamides.

The end compounds have therapeutical utility and find a use as anti-convulsant agents.

11 Claims, No Drawings

ANTI-CONVULSANT N-ETHANOLAMINE DIPHENYL ACETAMIDES

PRIOR ART

The prior art may be well illustrated by the French Pat. No. 2.176.473 (to Innothera) and Zh. Obshchei, Khimii 33 1570-1573 (1963)

SUMMARY OF THE INVENTION

The invention relates to novel acetamides and more accurately to diphenylacetamides having the formula I:

$$(B)_n \underset{X_2}{\overset{X_1}{\bigodot}} \underset{CH}{\overset{}{-}} \underset{X_4}{\overset{X_3}{\bigodot}} (A)_{n'}$$
$$CO\,NH-CH-CH-N\underset{R_5}{\overset{R_4}{\diagup}}$$
$$\phantom{CO\,NH-CH}Y\phantom{-CH}Z$$
(I)

in which $X_1$ and $X_3$, the same or different, is selected from the group consisting of a lower alkyl radical having from 1 to 6 carbon atoms, a lower alkyl radical and a lower alkylthio radical $X_2$ and $X_4$ the same or different, are hydrogen or a lower alkyl radical having from 1 to 6 carbon atoms A and B, the same or different, are a halogen, a lower alkyl radical or a lower alkoxy radical n and n' are integer from 0 to 3

Y and Z, the same or different, are hydrogen, a lower alkyl radical of 1 to 6 carbon atoms or one of each together with $R_4$ is an alkylene chain of 4 to 6 carbon atoms.

$R_4$ is hydrogen, a lower alkyl radical having from 1 to 6 carbon atoms or a benzyl radical.

$R_5$ is a lower alkyl radical having from 1 to 6 carbon atoms, a lower alkenyl having from 2 to 10 carbon atoms or an aryl lower alkyl radical, or $R_4$ and $R_5$ together are an alkylene chain of 4 to 5 carbon atoms one of which is optionally replaced with an imino radical of the formula $>N$ - R in which R is hydrogen, a lower alkyl radical of 1 to 6 carbon atoms, an acyloxylower alkyl radical, an alcoxylower alkyl radical or a hydroxylower alkyl radical.

The invention also relates to the salts of a compound of formula I with a mineral or organic acid.

This invention also discloses the optically-active isomers of a compound of formula I -when the alkyl side chain includes at least one asymetric carbon atom- and/or a salt thereof.

This invention provides further a process for producing the acetamides of formula I in which a substituted diphenyl acetic acid is reacted with an ethylene diamine derivative.

Moreover, this invention extends to the pharmaceutical compositions including as active ingredient at least a compound of formula I in admixture with an inert non-toxic pharmaceutical vehicle or carrier.

This invention concerns a method of treatment for epilepsy in human or veterinary medicine which comprise administering to said patients suffering from epilepsy a small but efficient amount of a compound of formula I.

PREFERRED EMBODIMENTS

The present invention relates to novel diphenyl acetamides and their obtention. The invention relates more precisely novel diphenylacetamides, the nitrogen of which is substituted with an amino alkyl chain.

The invention provides specifically novel diphenylacetamides having the general formula I $$(B)_n \underset{X_2}{\overset{X_1}{\bigodot}} \underset{CH}{\overset{}{-}} \underset{X_4}{\overset{X_3}{\bigodot}} (A)_{n'}$$
$$CO\,NH-CH-CH-N\underset{R_5}{\overset{R_4}{\diagup}}$$
$$\phantom{CO\,NH-CH}Y\phantom{-CH}Z$$
(I)

in which $X_1$ and $X_3$, the same or different, are a lower alkyl radical having from 1 to 6 carbon atoms a lower alkyl radical or a lower alkylthio radical $X_2$ and $X_4$ the same or different, are hydrogen or a lower alkyl radical having from 1 to 6 carbon atoms A and B, the same or different, are a halogen, a lower alkyl radical or a lower alkoxy radical n and n' are integer from 0 to 3

Y and Z, the same or different, are hydrogen, a lower alkyl radical of 1 to 6 carbon atoms or distinctly together with $R_4$ are an alkylene chain of 4 to 6 carbon atoms.

$R_4$ is hydrogen, a lower alkyl radical having from 1 to 6 carbon atoms or a benzyl radical.

$R_5$ is a lower alkyl radical having from 1 to 6 carbon atoms, a lower alkenyl having from 2 to 10 carbon atoms or an aryl lower alkyl radical.

or $R_4$ and $R_5$ together are an alkylene chain of 4 to 5 carbon atoms optionnally replaced with an imino radical of the formula $>N$ - R in which R is hydrogen, a lower alkyl radical of 1 to 6 carbon atoms, an acyloxylower alkyl radical, an alcoxylower alkyl radical or a hydroxylower alkyl radical.

Among the compounds of formula I they may be particularly cited -The compounds of general formula $I_A$ $$(B)_n \underset{X_2}{\overset{X_1}{\bigodot}} \underset{CH}{\overset{}{-}} \underset{X_4}{\overset{X_3}{\bigodot}} (A)_{n'}$$
$$CO\,NH-CH-CH-N\underset{R_5}{\overset{R_4}{\diagup}}$$
$$\phantom{CO\,NH-CH}R'\phantom{-CH}Z$$
($I_A$)

in which

A, B, $X_1$, $X_2$, $X_3$, $X_4$, n and n' are defined as previously given

R' is a lower alkyl radical having from 1 to 6 carbon atoms

Z is hydrogen, a lower alkyl radical or forms with $R_4$ the alkylene chain of a pyrrolidine or piperidine ring $R_4$ and $R_5$ the same or different are a lower alkyl radical having from 1 to 6 carbon atoms or together are the alkylene chain of a pyrrolidine or piperidine ring -The compounds of general formula $I_B$

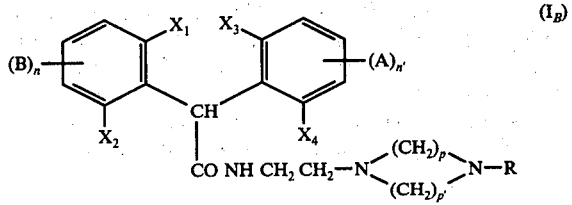

in which the substituents A, B, $X_1$, $X_2$, $X_3$, $X_4$, $n$ and $n'$ are defined as above indicated $p$ and $p'$ are integers, the sum of which is 3 or 4 and R is hydrogen, an alkyl radical having from 1 to 6 carbon atoms, a hydroxylower alkyl radical of 1 to 6 carbon atoms, a acyloxylower alkyl radical of 1 to 6 carbon atoms or a lower alkoxy lower alkyl radical of 1 to 6 carbon atoms.

-The compounds of general formula $I_C$

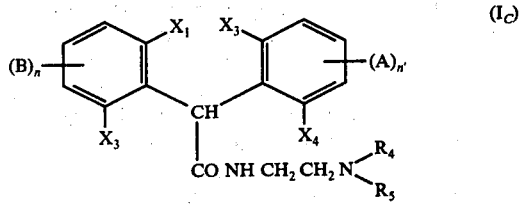

in which the substituents A, B, $X_1$, $X_2$, $X_3$, $X_4$ $n$ and $n'$ are defined as above $R_4$ and $R_5$, the same or different, are lower alkyl radicals having from 1 to 6 carbon atoms.

The compounds of general formula I may be as the free base or as a salt of addition with a mineral or organic acid, preferably a therapeutically-compatible acid. They may also contain an asymetric carbon. In this case, they may be resolved into their optically-active isomers.

As presently preferred compounds, they may be more specifically cited:
-dl N-(2-dimethylaminopropyl) α-(2,6-2',6'-tetramethyl diphenyl) acetamide and its methane sulfonic acid addition salt
-N-[2-(1-piperidino)ethyl] α-(2,6-2',6'-tetramethyl diphenyl) acetamide and its methanesulfonic acid addition salt
-N-[2-(4-methylpiperazinyl-1)ethyl] α-(2,6-2',6'-tetramethyl diphenyl) acetamide and its methanesulfonic acid addition salt
-N-[2(4-β-hydroxyethyl piperazinyl-1)ethyl] α-(2,6-2',6'-tetramethyldiphenyl) acetamide and its methanesulfonic acid addition salt
-N-(2-diethylaminoethyl) α-(2,6-2',6'-tetramethyldiphenyl) acetamide and its methanesulfonic acid addition salt The compounds of general formula I have interesting pharmacological properties. More precisely they are endowed with anti-convulsing activity and an anti-agressive activity. They have very slight toxicity and at the non-toxic dosages they have little neurodepressive activity.

They find accordingly a therapeutic use as anticonvulsive agent, namely as anti-epileptic drug in the treatment of the Petit Mal.

For the therapeutical use, they are employed in the form of pharmaceutical compositions incorporating as active ingredient at least a compound of general formula I together with an inert non-toxic pharmaceutical carrier. Moreover the pharmaceutical compositions may include a further agent having a similar or synergistic or complementary action. As example of such compounds they may be cited phenobarbital, trimethadione or phenacetylurea.

The used pharmaceutical compositions are those which are suitable for oral administration, parenteral administration, sublingual administration and rectal administration as for example tablets and coated tablets, dragees, soft gelatine capsules, drinkable solutions or suspensions, syrups, granules or drops, the injectible solutions packed in ampuls, phials, multidosis flasks, autoinjectibles syringes and carpules, sublingual tablets and suppositories.

The usual posology may broadly vary depending on the age, the weight of the patient the illness to be treated and the way of administration. It may range from 100 to 500 mg of active ingredient per unit dosage and from 200 to 1500 mg pro day, in the man.

The pharmaceutical compositions according to the invention are obtained according to the known methods of the pharmacology. They may incorporate as carriers, diluents or excipients, talc, magnesium stearate, lactose, mannitol, calcium carbonate, colloidal silica, titanium or aluminium oxyde for the dry compositions; water or saline solutions for the injectible preparations, cocoa butter or polyethylene glycol stearates for the suppositories.

They may also include fillers, extenders, tensioactive agents such as the mono oleate sorbitans known under the Trade Name of Tween or Span, the binders such as Methyl cellulose, Ethyl cellulose, Carboxymethyl cellulose or hydroxypropyl cellulose, jellifying or swelling agents such as starches, as polyacrylamides or alkali metal alginates.

Depending on the therapeutic use and the may of administration the percentage of active ingredient in the unit dosage will extend from 10 to 90 %.

This application also provides a process for producing the compounds of general formula I

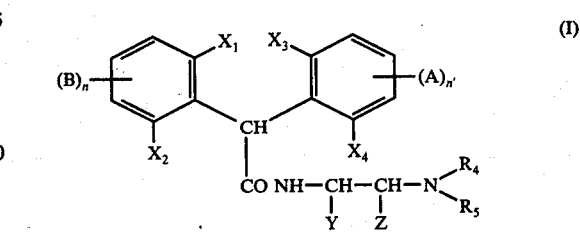

in which
$X_1$ and $X_3$ the same or different are a lower alkyl radical of 1 to 6 carbon atoms, a lower alkoxy, or a lower alkylthio
$X_2$ and $X_4$ the same or different are hydrogen, or a lower alkyl radical of 1 to 6 carbon atoms
A and B the same or different are a halogen, a lower alkyl of 1 to 6 carbon atoms or a lower alkoxy radical
$n$ and $n'$ are integers of 0 to 3
Y and Z, the same or different, are hydrogen, a lower alkyl radical of 1 to 6 carbon atoms, or together with $R_4$ form an alkylene chain of 4 to 6 carbon atoms
$R_4$ is a hydrogen, a lower alkyl radical of 1 to 6 carbon atoms or a benzyl radical $R_5$ is a lower alkyl radical of 1 to 6 carbon atoms, a lower alkenyl radical of 2 to 10 carbon atoms or a aryl lower alkyl radical or $R_4$ and $R_5$ together are an alkylene chain of 4 to 5 carbon atoms one of which may be replaced with an imino group $>N$ - R in which R is hydrogen, a lower alkyl radical of 1 to 6 carbon atoms a hydroxy lower alkyl radical, a lower alkoxy lower alkyl radical, or an acyloxy lower alkyl radical in which a diaryl acetic acid of the general formula II

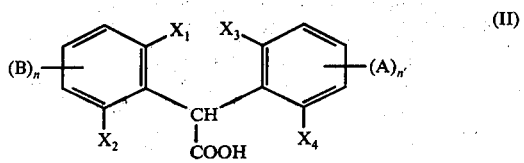

wherein the substituents A, B, $X_1$, $X_2$, $X_3$, $X_4$ n and n' have the above-given meanings or a functional derivative thereof is reacted with an ethylene diamine derivative of the general formula III

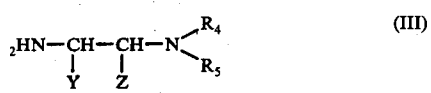

in which Y, Z, $R_4$ and $R_5$ are defined as above, to produce a diarylacetamide of the general formula I which may, when desired, by salified by adding a mineral or organic acid or when the molecule includes an asymetric carbon atom, be resolved into its optically-active isomers or when $R_4$ is a benzyl radical submitting it to hydrogenolysis or acidolysis in order to produce a compound of general formula I wherein $R_4$ is hydrogen.

The claimed process may also be defined along the following features:

(a) the condensation between the diarylacetic acid of formula II and the ethylene diamine derivative of formula III is performed in the presence of an agent activating the carboxylic function such as a dialkyl, or dicycloalkyl carbodiimide, ethoxyacetylene or an alkyl isonitrile.

(b) the functional derivative of the acid of general formula II is preferably a lower alkyl ester, an arylester, a halide, a symetric or mixed anhydride or an azide.

(c) the condensation between the ethylene diamine derivative of general formula III and the functional derivative of the diaryl acetic acid of general formula II is performed in the presence or in absence of a basic agent such as a pyridine base, for example pyridine or collidine, or a tertiary base for example a trialkyl amine or an aryl dialkyl amine.

(b) the hydrogenolysis of a compound of formula I wherein $R_4$ is a benzyl radical is performed in the presence of a catalyst based on a metal of the platinum family such as palladium or platinum.

(e) the imino group $>N$ - R in which R is hydrogen may be hydroxy alkylated by means of a halohydrin such as epichlorhydrin followed by hydrolysis of the oxirane ring or by means of an epoxyalkyl derivative such as ethylene oxyde or propylene oxyde.

(f) the imino group $>N$ - R in which R is a hydroxy lower alkyl radical may be acylated by means of a functional derivative of a carboxylic acid having up to 20 carbon atoms such as propionic acid, di n-propyl acetic acid, benzoic acid, 3, 4, 5-trimethoxy benzoic acid, nicotinic acid, 0-carbethoxy syringoic acid, nicotinic acid, stearoylglycolic acid, embonic acid, n-propyl thiazol 5-carboxylic acid.

(g) the imino group $>N$ - R in which R is a hydroxy lower alkyl may be alkylated by means of an alkylating reagent such an alkyl halide or an alkyl sulphate optionally in the presence of a basic agent such as silver oxyde or silver carbonate.

(h) the resolution step may be performed using an optically-active carboxylic acid such as dibenzoyl d-tartaric acid or d-camphoric acid; an optically-active sulphonic acid such as d-camphosulphonic acid; or an optically-active phosphoric acid such as d-glucose 1-phosphoric acid or d-glucose 1,6-diphosphoric acid. It may also be possible to start from an ethylene diamine derivative of general formula III previously resolved to produce an optically-active isomer of general formula I.

(i) the step of salification may be performed in adding to the free base an organic or mineral acid such as hydrochloric acid, sulphuric acid, acetic acid, benzoic acid, salicylic acid, 5-thiazol carboxylic acid, 5-pyrrolidinone carboxylic acid, tartaric acid, pyruvic acid, benzene sulphonic acid or embonic acid. As far as the invention is concerned the term lower alkyl radical encompasses any alkyl radical having from 1 to 6 carbon atoms in straight or branched chain such as methyl, ethyl, isopropyl, terbutyl, sec.butyl, neo pentyl and n-hexyl. The term lower alkenyl radical encompasses any ethylenic chain having from 2 to 10 carbon atoms such as allyl, methallyl, dimethyl allyle, isopentenyl, butenyl, buta 1,4-dienyl and triallyl methyl. When $R_4$ and $R_5$ together represent an alkylene chain of 4 to 5 carbon atoms, they form with the nitrogen atom to which they are bound a nitrogenous hetero cycle such as pyrrolidine and piperidine. When they incorporate an imino radical, they form a pyrazoline or piperazine ring. Further these hetero cycles may be substituted by one or several lower alkyl radicals. The term aryl is intended to designate an unsubstituted phenyl ring or a phenyl ring substituted with no more that three substituents selected from the group consisting of halogen, lower alkoxy, lower alkylthio, trifluoromethyl, alkylenedioxy, hydroxy and lower alkyl such as 3,4-dimethoxyphenyl, 2,4-dichlorophenyl, m.trifluoromethyl phenyl, 3,4,5 -trimethoxyphenyl, syringyl, 2,6-dimethylphenyl and veratryl. The term "aryl lower alkyl" is intended to designate an aryl radical defined as above, bearing a lower alkyl radical such as m.trifluoromethyl benzyle, 3,4-dimethoxybenzyl, α-methylbenzyl, phenylethyl, phenylpropyl, β-methylphenylethyl, p.chlorobenzyl, methylene dioxy benzyl and benzyl.

The starting diarylacetic acids of general formula II may obtained according to the process described in the French Pat. No. 2.221.144. The ethylene diamine derivatives of general formula III are known products. They are conveniently produced by condensing a (β-bromoalkyl) phthalimide with a primary or secondary alkyl or cycloalkyl amine then hydrazinolyzing the N-(β-aminoalkyl) phtalimide thus produced.

The following examples are merely intended to illustrate the invention without limiting it. The temperature are expressed in degrees Centigrade.

EXAMPLE 1

N-[(N'-ethylpyrrolidinyl-2) methyl]
α-(2,6-2',6'-tetramethyldiphenyl) acetamide

In a three-neck flask fitted with a mechanical stirring device, they are successively poured 3.8 g of 1-ethyl 2-aminomethylpyrrolidine then 4.2ml triethylamine and 25ml ethyl ether. The mixture is kept in cold water to maintain the temperature at about + 10° C and is added with a solution of 8.6 g (2,6-2′,6-tetramethyldiphenyl) acetyl chloride in 25ml ethyl ether. The stirring is also maintained during the addition and for two further hours. Once the acid chloride added, the reaction mixture is let to revert to room temperature.

The suspension formed during the reaction time is made basic by adding thereto 100ml of a 2N sodium hydroxyde solution. After mixing, the etherous phase is separated and the aqueous phase is exhausted with ether. The etherous solutions are gathered, washed with water, dried on magnesium sulphate and filtered, then evaporated off under reduced pressure. The dry residue is recovered, giving a yield of 10.4g. The raw material is further purified by recrystallizing it from cyclohexane-N-[(N′-ethyl pyrrolidinyl-2) methyl] α-(2,6-2′,6′-tetramethyl diphenyl acetamide is obtained in pure form melting at 188°. It is soluble in aqueous hydrochloric acid giving rise to the production of the hydrochloride by evaporation of the solvent.

Analysis : $C_{25}H_{34}N_2O = 378.56$

| | C | H | N% |
|---|---|---|---|
| Calculated | 79.32 | 9.05 | 7.40 |
| Found | 79.09 | 9.11 | 7.43 |

EXAMPLE 2 dl N-[2-(dimethylamino) propyl] α-(2,6-2′,6′tetramethyl diphenyl)acetamide

Using the same process as in example 1 and starting from 3.05g dl 2-dimethylamino propylamine 6.6g of pure compound are obtained after recrystallization from petroleum ether. It melts at 100°. The yield amounts to 70% dl N-[2-(dimethylamino) propyl] α-(2,6-tetramethyl diphenyl) acetamide is soluble in an aqueous solution of methane sulphonic acid and the methane sulfonate is obtained after evaporation of the solvent Analysis : $C_{23}H_{32}N_2O = 352.51$

| | C | H | N% |
|---|---|---|---|
| Calculated | 78.37 | 9.15 | 7.95 |
| Found | 78.40 | 8.90 | 7.95 |

EXAMPLE 3

N-(2-diethylaminoethyl) α(2,6-2′,6′-tetramethyldiphenyl) acetamide.

Using the same process as in example 1 and starting from 3.48g of NN-diethyl ethylenediamine, 9.2g of raw material are obtained, the melting point of which is about 100°.

After recrystallization from n-pentane, 8.9g of N-(2-diethylaminoethyl) α-(2,6-′,6′-tetramethyldiphenyl) acetamide are isolated, melting at 103°.

The yield in pure product amounts to 82%.

Analysis : $C_{24}H_{34}N_2O = 366.55$

| | C | H | N% |
|---|---|---|---|
| Calculated | 78.64 | 9.35 | 7.64 |
| Found | 78.25 | 9.26 | 7.63 |

N(2-diethylaminoethyl)α-(2,6-2′,6′-tetramethyldiphenyl) acetamide is soluble in the stoichiometric amount of methane sulphonic acid in water.

By evaporating off the solvent, the methane sulphonate is recovered.

EXAMPLE 4

N[2-(piperidino-1) ethyl] α-(2,6-2′,6′-tetramethyldiphenylacetamide.

Using the process of example 1 and starting from 2.3g of N(2-aminoethyl) piperidine, 6.6g of raw micro-cristalline product is obtained. It is further purified by recrystallizing it from petroleum ether and 3.6g of pure N[2-(piperidino-1) ethyl] α-(2,6-2′,6′-tetramethyl diphenyl) acetamide is obtained which melts at 107°.

Analysis : $C_{25}H_{34}N_2O = 378.56$

| | C | H | N% |
|---|---|---|---|
| Calculated | 79.32 | 9.05 | 7.40 |
| Found | 79.36 | 9.04 | 7.37 |

The product may be dissolved in an aqueous solution of methane sulphonic acid from which the methane sulphonate is recovered.

EXAMPLE 5

N[2-(4-methyl piperazinyl-1) ethyl] α(2,6-2′,6-tetramethyl diphenyl) acetamide.

Using the process of example 1 and starting from 7.45g α(2,6-2′,6-tetramethyl diphenyl) acetyl chloride and 3.7 g N-methyl N′-(β-aminoethyl) piperazine, they are obtained 3.1g N[2-(4-methyl piperazinyl-1) ethyl] α-(2,6-2′,6′ tetramethyl diphenyl) acetamide after recrystallization from cyclohexane. The yield amounts to 30%. This compound melts at 114°.

Analysis : $C_{25}H_{35}N_3O_4 = 393{,}58$

| | C | H | N% |
|---|---|---|---|
| Calculated | 76.29 | 8.96 | 10.68 |
| Found | 76.05 | 9.14 | 10.54 |

The compound may be dissolved in an aqueous solution of methane sulphonic acid from which the methane sulphonate is recovered.

EXAMPLE 6

N[4-(2-hydroxyethyl) piperazinyl-1] ethyl α-(2,6-2′,6′-tetramethyldiphenyl) acetamide.

Using the same process as in example 1 and starting from 6.15g of α-(2,6-2,′6′ tetramethyl diphenyl acetyl chloride and 3.4g 4-(β hydroxyethyl) 1-(β-aminoethyl) piperazine, 4.7g of the title compound are obtained after recrystallization from isopropyl acetate. The pure compound melts at 138°–139°. The yield is 51.5% of the theory.

Analysis : $C_{26}H_{37}N_3O_2 = 423.6$

| | C | H | N% |
|---|---|---|---|
| Calculated | 73.72 | 8.81 | 9.92 |
| Found | 73.55 | 8.61 | 9.72 |

This compound is soluble in dilute aqueous methane sulphonic acid. After evaporation of the solvent the methane sulphonate is recovered.

By treating N[4-(2-hydroxyethyl) piperazinyl-1] ethyl α-(2,6-2',6'-tetramethyl diphenyl) acetamide with acetic acid anhydride in the presence of pyridine, N[4-(2-acetoxyethyl) piperazinyl-1] ethyl α-(2,6-2',6'-tetramethyl diphenyl) acetamide is obtained.

By treating N[4-(2-hydroxyethyl) piperazinyl-1] ethyl α-(2,6-2',6'-tetramethyl diphenyl) acetamide with methyl iodide in acetone in the presence of silver oxyde, N[4-(2-methoxyethyl) piperazinyl-1] ethyl α(2,6-2',6'-tetramethyl diphenyl) acetamide is produced.

In a similar manner starting from α-bis (2,4-diterbutyl 6-methyl) diphenyl acetic acid-obtained according to O. Akkerman Rec. Trav. Chim. Pays-Bas 86, 1018 (1967) and 4-(β-hydroxyethyl) 1-(β-aminoethyl) piperazine, N[4-(2-hydroxyethyl) piperazinyl-1] ethyl α-(2,4-2',4'-tetratertbutyl 6,6'-dimethyl) diphenyl acetamide is recovered.

EXAMPLE 7

Pharmacological study of the compounds of general formula I.

(a) acute toxicity

The average letal dosis of the compounds of general formula I have been determined on lots of 10 male mice (strain CD) by administering intraperitoneously increasing amounts of each compound. The animals are kept under survey for 8 days and the deaths, if any, are numbered. The average letal dosis is graphically determined. Depending on the compound, the average letal dosis range from 100 to 150mg/kg by intraperitoneous way. At the subletal dosis the animals show a decrease of the motility and of the muscular tone. At the toxic dosis the animal die in a convulsive state.

(b) Protection against convulsions caused by the electroshock.

Convulsions occured on batches of mice by submitting them to an electric shock caused by an electric discharge of 100V/300Hz for 110ms. An hour before the electroshock, all the batches but one, are administered with the compound to be tested by intraperitoneous way, suspend in an aqueous solution of arabic gum. A batch of controls receives only the solution of arabic gum in a volume of 0.5ml/kg. The used dosis range from 12.5mg to 70mg/kg. An avery protection (i.e. a protection of 50%) is obtained with a dosis of 30 to 50mg/kg depending on the tested compound.

(c) Protection against seizure provoked by pentamethylene tetrazole.

The injection of pentamethylene tetrazole provokes a strong spasm in which the limbs are maximally extended. Inhibiting this spasm allows the measure of the anti-convulsant activity of the compounds of general formula I. These compounds are administered to lots of mice through intraperitoneal way at a dosis ranging from 25 to 75mg/kg one hour before the injection through the same way of 100mg/kg pentamethylene terazole. The increase of the delay for appearing the convulsions and the decrease of the percentage of clonic convulsions in the controls are used to determine the degree of protection. Namely the delay in the occurance of the convulsions is increased of 25 to 175%.

(d) Inhibitory effect on aggressiveness

The anti-aggressivity test is performed on isolated mice or on isolated male rats previously bulbectomized (i.e. having be submitted to the ablation of the olfactive bulbs) according to the method described by L. Valzelli and co. workers in Aggressive Behaviour 1969 p.70) 76 (Excerpta Medica Foundation (Amsterdam) and by P. Karli and co-workers in Aggressive Behaviour 1969 pp. 47–55. At a dosis of 10 to 50mg/kg in the mice through intra peritoneous way, the compounds of general formula I decrease from 20 to 100% the number of attacks against the other animals and the score of aggressiveness. In the rat doses of 25 and 50mg/kg through intraperitoneal way, decrease the number of animal killers from 100% (controls) to about 40% (treated animals).

EXAMPLE 8

Pharmaceutical compositions incorporating a compound of general formula I

Tablets containing 0.250g of dl N-[2(dimethylamino) propyl] α-(2,6-2',6'tetramethyl diphenyl) acetamide dl N-[2(dimethylamino) propyl] α-(2,6-2',6'-tetramethyldiphenyl) acetamide: 250g
Mais startch: 120g
Calcium Carbonate: 40g
Magnesium Stearate: 15g
Talc: 60g
Methyl cellulose: 5g
Ethyl cellulose: 10g
for 1000 tablets of a final weight of about 0.500g.

What we claim is:

1. A compound having the formula

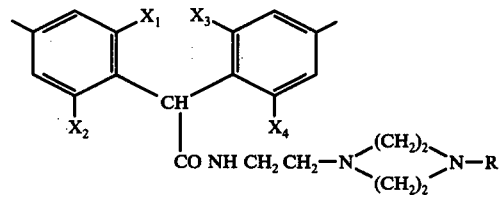

in which $X_1$, $X_2$, $X_3$, and $X_4$ are the same or different and are selected from the group consisting of a lower alkyl radical having from 1 to 6 carbon atoms R is hydrogen, an alkyl radical having from 1 to 6 carbon atoms, a hydroxylower alkyl radical of 1 to 6 carbon atoms, a acyloxylower alkyl radical of 1 to 6 carbon atoms or a lower alkoxy lower alkyl radical of 1 to 6 carbon atoms.

2. A compound according to claim 1 wherein $X_1$ and $X_3$ are methyland $X_2$ and $X_4$ are methyl or tert.butyl and R is hydroxyethyl, acetoxyethyl, or methoxyethyl 3. N[4-(2-acetoxyethyl) piperazinyl-1] ethyl-(2,6-2',6'-tetramethyl diphenyl) acetamide, a compound of claim 2.

4. N[4 (2 methoxyethyl) piperazinyl-1] ethyl (2,6 2',6'-tetramethyl diphenyl)acetamide, a compound of claim 2.

5. N[4-(2 hydroxyethyl) piperazinyl-1] ethyl (2,4-2',4'-tetratertbutyl 6,6'-dimethyl) diphenyl acetamide.

6. A compound according to claim 1 selected from the group consisting of -N-[2(4- β-hydroxyethyl piperazinyl-1) ethyl] α-(2,6-2',6'-tetramethyldiphenyl) acetamide and its methanesulfonic acid addition salt.

7. An anti-convulsively active pharmaceutical composition comprising a safe but anti-convulsively effective amount of at least one compound of claim 1 in admixture with an inert non-toxic pharmaceutically acceptable carrier.

8. The pharmaceutical composition according to claim 7 in which the carrier is adapted for the oral, parenteral, sublingual or rectal ways.

9. A pharmaceutical composition according to claim 7 in which the amount of active ingredient ranges from 100 to 500 mg per unit dosage.

10. A method for treating epilepsy in the man or in the animals suffering from said illness which consists in administering to the patients a small but effective amount of a compound of claim 1.

11. The method of treatment of claim 10 in which the small but effective amount of the compound administered therein ranges from 3.33 mg/kg to 25 mg/kg per day.

* * * * *